United States Patent [19]

Funahashi et al.

[11] Patent Number: 4,814,475
[45] Date of Patent: Mar. 21, 1989

[54] VINYL SILANE COMPOUNDS

[75] Inventors: Yuichi Funahashi; Junichiro Watanabe; Kiyoshi Takeda; Makoto Matsumoto, all of Ohta, Japan

[73] Assignee: Toshiba Silicone Co., Ltd., Japan

[21] Appl. No.: 242,007

[22] Filed: Sep. 8, 1988

[30] Foreign Application Priority Data

Sep. 28, 1987 [JP] Japan .................. 62-240956

[51] Int. Cl.$^4$ .............................................. C07F 7/08
[52] U.S. Cl. .................................................. 556/489
[58] Field of Search ........................................ 556/489

[56] References Cited

U.S. PATENT DOCUMENTS

| | | | |
|---|---|---|---|
| 3,334,122 | 8/1967 | Cekada et al. | 556/489 X |
| 3,423,445 | 1/1969 | Holbrook et al. | 556/489 X |
| 4,100,172 | 7/1978 | Mui et al. | 260/327 |
| 4,242,272 | 12/1980 | Koga et al. | 556/489 |
| 4,642,356 | 2/1987 | Langner et al. | 556/489 X |
| 4,722,975 | 2/1988 | Itoh et al. | 525/288 |

FOREIGN PATENT DOCUMENTS

| | | | |
|---|---|---|---|
| 60-88015 | 5/1985 | Japan | 556/489 UX |
| 60-90205 | 5/1985 | Japan | 556/489 UX |
| 61-127764 | 6/1986 | Japan | 556/489 UX |
| 61-127711 | 6/1986 | Japan | 556/489 UX |
| 62-13447 | 1/1987 | Japan | 556/489 UX |

*Primary Examiner*—Paul F. Shaver

[57] ABSTRACT

A vinylsilane compound represented by general formula (I):

$$R^1CH_2CH_2SiR_a^2(CH=CH_2)_{3-a} \qquad (I)$$

wherein $R^1$ represents a monovalent alicyclic unsaturated hydrocarbon group selected from the group consisting of a cyclohexenyl group and a bicycloheptenyl group; $R^2$ represents a monovalent hydrocarbon group free from an aliphatic unsaturated bond; and a represents 1 or 2, is herein disclosed.

7 Claims, No Drawings

VINYL SILANE COMPOUNDS

The present application claims the priority of Japanese patent application Ser. No. 62-240956 filed on Sept. 28, 1987.

BACKGROUND OF THE INVENTION

The present invention relates to novel organic silicon compounds and more particularly, to novel silane compounds containing an alicyclic hydrocarbon group having a carbon-carbon double bond in the ring thereof and a vinyl group bound to the silicon atom in the molecule thereof.

Organic silicon compounds having two kinds of functional groups in the same molecule thereof are known and utilize the reactivity of each functional group or difference in the reactivity. They are used as silane coupling agents or as raw materials for various chemical substances; monomers for producing silicon-containing high molecular weight compounds, crosslinking agents, modifiers, or the like. For example, organic silicon compounds used as silane coupling agents possess a carbon functional group capable of binding to an organic material and a silicon functional group capable of reacting with and binding to an inorganic material and are interposed at the interface between the organic material and the inorganic material to function to firmly bind both with each other.

However, hitherto known organic silicon compounds having two functional groups in the same molecule thereof are mostly those having a hydrolyzable group such as an alkoxy group as the silicon functional group. Where organic compounds are used to bind with each other, the hydrolyzable silicon-oxygen-carbon bond remains in the product so that problems of poor moisture resistance, etc. may be encountered. Thus, there might be a limitation depending upon purpose of use.

Recently, a variety of monomers having a vinylsilyl group and a polymerizable ethylenic double bond in the same molecule have been proposed (Published Unexamined Japanese Patent Application Laid Open Nos. 60-88015, 60-90205, 61-127711, 61-127764 and 62-13447). As organic groups having the ethylenic double bond in these monomers, there are disclosed a vinylphenyl group, a methacrylic acid group, an acrylic acid group, etc. that have a higher polymerization reactivity; and a vinyl group, a propenyl group, a vinyloxy group, a vinylpyridyl group, etc. that have a somewhat poor polymerization reactivity. However, the former is handled only with difficulty because homopolymerization tends to easily occur due to radical reaction induced by heat or light. On the other hand, the latter has an insufficient difference in reactivity from the vinylsilyl group so that the reaction properties of both double bonds cannot be effectively utilized. It is thus desirable to develop vinylsilyl group-containing monomers with novel organic groups having a sufficient difference in the reactivity between the ethylenic double bond and the vinylsilyl group, having a low homopolymerization tendency when exposed to heat or light but effective for preparation of silicon-containing high molecular weight compounds.

SUMMARY OF THE INVENTION

An object of the present invention is to provide novel silane compounds free from any hydrolyzable group in the molecule thereof by incorporating two kinds of carbon-carbon double bonds each having different reactivities in the molecule thereof, and suited for use in coupling between organic compounds or, preparing, modifying or crosslinking, various organic compounds or silicon-containing high molecular weight compounds.

As a result of extensive investigations in an attempt to obtain organic silicon compounds suited for the foregoing object, the present inventors have synthesized organic silicon compounds (I) having as a carbon functional group a monovalent alicyclic hydrocarbon group with a carbon-carbon double bond in the ring thereof and having as a silicon functional group, a vinyl group bound to the silicon atom.

The present invention lies in a vinylsilane compound represented by the general formula (I):

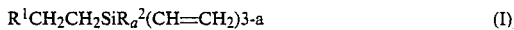

$$R^1CH_2CH_2SiR_a^2(CH=CH_2)_{3-a} \qquad (I)$$

wherein $R^1$ represents a monovalent alicyclic unsaturated hydrocarbon group selected from the group consisting of a cyclohexenyl group and a bicycloheptenyl group; $R^2$ represents a monovalent hydrocarbon group free from an aliphatic unsaturated bond; and a represents 1 or 2.

$R^1$ is a cyclohexenyl group or a bicycloheptenyl group that is a monovalent alicyclic hydrocarbon group having a carbon-carbon unsaturated bond in the alicyclic ring thereof. Examples of such $R^1$ include a 2-cyclohexenyl group, 3-cyclohexenyl group, 5-norbornenyl group, 2-norpinenyl group, etc. Among them, 2-cyclohexenyl group, 3-cyclohexenyl group and 5-norbornenyl group are preferred in view of easy accessibility and easy synthesis of raw materials from an industrial standpoint and appropriate reactivity in the carbon-carbon double bond in the alicyclic ring.

$R^2$ is a monovalent hydrocarbon group free from an aliphatic unsaturated bond. Examples include various hydrocarbon groups, for example, an alkyl group such as methyl group, ethyl group, propyl group, butyl group, etc.; a cycloalkyl group such as cyclohexyl group; an aryl group such as phenyl group; an aralkyl group such as β-phenylethyl group or β-phenylpropyl group; etc. In view of easy accessibility and easy synthesis of raw materials, as well as excellent heat stability of silicon-containing high molecular weight compounds derived using the vinylsilane compounds, etc., the alkyl group or phenyl group is preferred. Particularly preferred is the methyl group.

When $R^2$ is two, they may be different from each other or may be the same.

Symbol "a" is 1 or 2 but 2 is preferred.

The vinylsilane compound of the present invention can be obtained, for example, by reacting an aliphatic hydrocarbon compound having a vinyl group in the side chain and a carbon-carbon double bond in the alicyclic ring, represented by general formula (II):

$$R^1 CH=CH_2 \qquad (II)$$

wherein $R^1$ is as defined above, with a hydrochlorosilane compound represented by general formula (III):

$$HSiR_a^2Cl_{3-a} \qquad (III)$$

wherein $R^2$ and a are as defined in formula (I), in the presence of a platinum catalyst at a temperature of 50° to 80° C. thereby causing selective hydrosilylation on the vinyl group on the side chain to form an alicyclic chlorosilane compound having the carbon-carbon double bond in the alicyclic ring, represented by general formula (IV):

$$R^1CH_2CH_2SiR_a{}^2Cl_{3-a} \qquad (IV)$$

wherein $R^1$, $R^2$ and a are as defined above; and reacting this compound (IV) with a vinyl magnesium halide to replace the vinyl group for the chlorine atom bound to the silicon atom through the Grignard reaction to give the desired vinylsilane compound (I).

The organic vinylsilane compound of the present invention possesses the strained carbon-carbon double bond contained in the alicyclic ring thereof as the carbon functional group and the vinyl group bound to the silicon atom as the silicon functional group in the molecule thereof and are thus useful as raw materials for organic synthesis of various chemical substances, raw materials of silicon-containing high molecular weight compounds, modifiers, or coupling agents between organic materials, etc. utilizing the reactivities of or difference in the reactivities between these functional groups.

The vinylsilane compound of the present invention has no hydrolyzable group in the molecule itself. Accordingly, using the vinylsilane compound as a starting raw material, a coupling agent, a modifier, etc., other organic silicon compounds having no hydrolyzable property, silicon-containing high molecular compounds, etc. can easily be obtained.

EXAMPLES

Hereafter the present invention will be described in more detail by referring to the examples but is not deemed to be limited only to these examples. Parts and % are all by weight, unless otherwise indicated.

Example 1

To a flask equipped with a dropping funnel were charged 150 parts of 2-vinyl-5-norbornene and 0.1 part of a solution of chloroplatinic acid in isopropanol (containing 2% as a platinum atom) were charged. While heating to 70° C., 136 parts of dimethylchlorosilane were added dropwise to the mixture and reacted at 70° C. for an hour. Distillation was performed under reduced pressure to give 195 parts of 2-(5-norbornenyl)ethyldimethylchlorosilane.

Next, a flask similarly equipped with a dropping funnel was inerted with a nitrogen atmosphere and then 360 parts of a 2.5 N tetrahydrofuran solution of vinyl magnesium bromide were charged. While keeping the temperature at 10° C., 171 parts of the aforesaid 2-(5-norbornenyl) ethyldimethylchlorosilane were charged over 30 minutes. After completion of the dropwise addition, the temperature was elevated to room temperature and allowed to react for an hour. The reaction mixture was cooled to 0° C. and 300 parts of a 1:1 mixture of n-hexane and diethyl ether and then 30 parts of a saturated aqueous solution of ammonium chloride were added thereto. 1 N hydrochloric acid aqueous solution was then added thereto until the system was neutralized. Fractionation was performed to collect the organic phase. The organic phase was washed with a saturated aqueous saline solution and dried over Glauber's salt. The system was distilled under reduced pressure to give 151 parts of the reaction product showing a boiling point of 78° C./1 Torr.

The molecular weight of the reaction product was determined by gas mass spectral analysis. Further elemental analysis was conducted and infrared absorption spectrum (IR) and 1H-NMR spectrum were determined. The results of these measurements and attribution of the spectra are as shown in Table 1.

TABLE 1

| | |
|---|---|
| Molecular weight | 206 |
| Elemental analysis (%) | C 75.92 (75.85) |
| Figures with parenthesis | H 10.62 (10.74) |
| indicate calculated values. | Si 13.46 (13.61) |
| IR (liquid film method$\nu$(cm$^{-1}$) | 2950, 1296, 828, 520 |
| $^1$H—NMR (90 MHz; CCl$_4$) $\delta$(ppm) | 0.01 (s, 6H, Si(C$\underline{H}_3$)$_2$) 0.34-0.74 (m, 3H, SiC$\underline{H}_2$—, 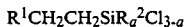 ) 0.91-1.58 |
| | (m, 4H, 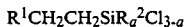 ) 1.68-2.17 |
| | (m, 2H, 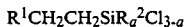 ) |
| | 2.80 (bs, 2H, 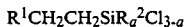 ) |
| | 5.46-6.39 (m, 5H, 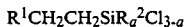, Si—C$\underline{H}$=C$\underline{H}_2$) |

From the results of these analyses, it was verified that the obtained product was 2-(5-norbornenyl) ethyldimethylvinyl-silance having the following structural formula.

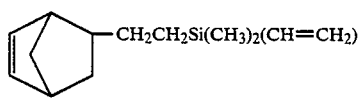

The yield to the theoretical yield was 67% based on 2-vinyl-5-norbornene.

Example 2

237 parts of a 2-(3-cyclohexenyl)ethyldimethylchlorosilane showing a boiling point of 86° C./4 Torr were obtained in a manner similar to Example 1 except that 152 parts of 2-vinylcyclohexene were used in place of 2-vinyl-5-norbornene and the amount of dimethylchlorosilane was changed to 142 parts.

Next, using 162 parts of the aforesaid silane compound, Grignard reaction and post treatment were carried out in a manner similar to Example 1. The system was distilled under reduced pressure to give 143 parts of the reaction product having a boiling point of 82° C./3 Torr.

With the reaction product, analysis was performed as in Example 1. The results and attribution are as shown in Table 2.

TABLE 2

| Molecular weight | 194 |
|---|---|
| Elemental analysis (%) Figures with parenthesis indicate calculated values. | C 74.39 (74.14) H 11.30 (11.41) Si 14.31 (14.45) |
| IR (liquid film method)ν(cm$^{-1}$) | 2910, 1246, 834, 512 |
| $^1$H—NMR (90 MHz; CCl$_4$) δ(ppm) | 0.07 (s, 6H, Si(C$\underline{H}_3$)$_2$) 0.42–0.78 (m, 2H, —C$\underline{H}_2$—Si,) 100–1.58 (br, 4H, ...) 1.58–1.78 (br, 1H, ...) 1.75–2.32 (br, 4H, ...) 5.47–6.40 (m, 5H, ...Si—C$\underline{H}$=C$\underline{H}_2$) |

From the results of these analyses, it was verified that the obtained product was 2-(3-cyclohexenyl)ethyldimethylvinyl-silane having the following structural formula.

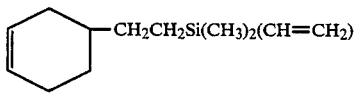

The yield to the theoretical yield was 77% based on 2-vinylcyclohexene.

Example 3

258 parts of a reaction product showing a boiling point of 142° C./1 Torr was obtained in a manner similar to Example 1 except that 219 parts of diphenylchlorosilane was used in place of dimethylchlorosilane.

The molecular weight of the reaction product by gas mass spectral analysis, the results of elemental analysis, and IR and 1H-NMR spectra and their attribution are as shown in Table 3.

TABLE 3

| Molecular weight | 331 |
|---|---|
| Elemental analysis (%) Figures with parenthesis indicate calculated values. | C 83.76 (83.58) H 7.83 (7.92) Si 8.41 (8.50) |
| IR (liquid film method )ν (cm$^{-1}$) | 2950, 1428, 1115, 700 |
| $^1$H—NMR (90 MHz; CCl$_4$) δ(ppm) | 0.36–0.70 (m, 3H, Si—C$\underline{H}_2$—, ...) 0.90–1.62 (m, 4H, ...) 1.70–2.20 (m, 2H, ...) 2.80 (bs, 2H, ...) 5.46–6.39 (m, 5H, ...Si—C$\underline{H}$=CH$_2$) 6.73–7.63 (m, 10H, Si(C$_6$H$_5$)$_2$) |

From the results of these analyses, it was verified that the obtained product was 2-(5-norbornenyl) ethyldiphenylvinyl-silane having the following structural formula.

—CH$_2$CH$_2$Si(C$_6$H$_5$)$_2$(CH=CH$_2$)

The yield to the theoretical yield was 78% based on 2-vinyl-5-norbornene.

Example 4

Hydrosilylation was performed followed by distillation under reduced pressure in a manner similar to Example 1 except that 152 parts of methyldichlorosilane were used in place of dimethylchlorosilane and the amount of isopropanol solution of chloroplatinic acid was 0.1 part. Thus, 154 parts of a 2-(3-cyclohexenyl)ethylmethyldichlorosilane showing a boiling point of 75° C./3 Torr were obtained.

Next, using 154 parts of the aforesaid silane compound, a Grignard reaction and post treatment were carried out in a manner similar to Example 1 except that the amount of 2.5 N vinylmagnesium bromide tetrahydrofurane solution was 607 parts. The system was distilled under reduced pressure to give 157 parts of the reaction product having a boiling point of 85° C./3 Torr.

Analysis was performed on the reaction product as in Example 1. The results and attribution are as shown in Table 4.

TABLE 4

| | |
|---|---|
| Molecular weight | 206 |
| Elemental analysis (%) Figures with parenthesis indicate calculated values. | C 75.90 (75.65 H 10.63 (10.74) Si 13.47 (13.61) |
| IR (liquid film method)ν(cm$^{-1}$) | 2910, 1245, 837, 513 |
| $^1$H—NMR (90 MHz; CCl$_4$) δ(ppm) | 0.09 (s, 3H, Si—CH$_3$) 0.42–0.80 (m, 2H, SiCH$_2$—,) 0.97–1.63 |

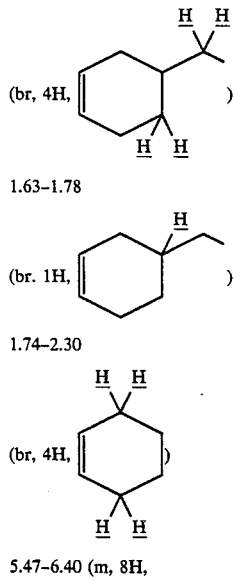

(br, 4H, )

1.63–1.78

(br. 1H, )

1.74–2.30

(br, 4H, )

5.47–6.40 (m, 8H,

TABLE 4-continued

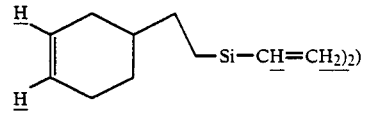

—Si—CH=CH$_2$)$_2$)

From the results of these analyses, it was verified that the obtained product was 2-(3-cyclohexenyl)ethylmethyldivinyl-silane having the following structural formula.

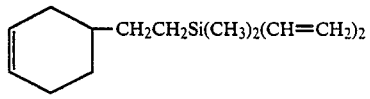

—CH$_2$CH$_2$Si(CH$_3$)$_2$(CH=CH$_2$)$_2$

The yield to the theoretical yield was 76% based on 2-vinylcyclohexene.

While the invention has been described in detail and with reference to specific embodiments thereof, it is apparent to one skilled in the art that various changes and modifications can be made therein without departing from the spirit and the scope of the present invention.

What is claimed is:

1. A vinylsilane compound represented by the general formula (I):

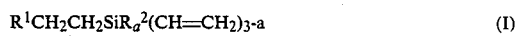

R$^1$CH$_2$CH$_2$SiR$_a^2$(CH=CH$_2$)$_{3-a}$     (I)

wherein R$^1$ represents a monovalent alicyclic unsaturated hydrocarbon group selected from the group consisting of a cyclohexenyl group and a bicycloheptenyl group; R$^2$ represents a monovalent hydrocarbon group free from any aliphatic unsaturated bond; and a represents 1 or 2.

2. A vinylsilane compound as claimed in claim 1, wherein R$^1$ is a 2-cyclohexenyl group or a 3-cyclohexeyl group.

3. A vinylsilane compound as claimed in claim 1, wherein R$^1$ is a 5-norbornenyl group.

4. A vinylsilane compound as claimed in claim 1, wherein R$^2$ is an alkyl or a phenyl group.

5. A vinylsilane compound as claimed in claim 1, wherein R$^2$ is methyl group or phenyl group.

6. A vinylsilane compound as claimed in claim 1, wherein R$^2$ is methyl group.

7. A vinylsilane compound as claimed in claim 1, wherein a is 2.

* * * * *